United States Patent

Skobeltzin et al.

[11] Patent Number: 6,124,087
[45] Date of Patent: Sep. 26, 2000

[54] METHOD OF DIAGNOSING A MALIGNANT DISORDER OR ITS PRECURSOR STAGES

[75] Inventors: Evguenia Skobeltzin, Karlsruhe; Ilya Krouglikov, Eggenstein-Leopoldshafen; Gudrun Knedlitschek, Karlsruhe; Karl-Friedrich Weibezahn, Stutensee; Hermann Dertinger, Heidelberg, all of Germany

[73] Assignee: Forschungszculrum Kovisruhe GmbH, Karlsruhe, Germany

[21] Appl. No.: 09/053,544

[22] Filed: Apr. 3, 1998

Related U.S. Application Data

[63] Continuation-in-part of application No. PCT/EP96/04416, Oct. 11, 1996.

[30] Foreign Application Priority Data

Oct. 27, 1995 [DE] Germany ............ 195 40 006

[51] Int. Cl.⁷ .............. A01N 1/02; C12Q 3/00; C12Q 1/08; G01N 1/30
[52] U.S. Cl. ............ 435/2; 435/40.5; 435/40.51; 435/3
[58] Field of Search ............ 435/2, 40.5, 40.51, 435/3

[56] References Cited

U.S. PATENT DOCUMENTS 4,788,155 11/1988 Pasula.

OTHER PUBLICATIONS

K. Riggs, et al. "Alterations in Circulating Lymphocyte Number and Function AFTE Circulation Through Colorectal Carcinomas", Aug. 20, 1990, *Surgery*, vol. 109, No. 6.

*Primary Examiner*—Yvonne Eyler
*Assistant Examiner*—Lin Sun-Hoffman
*Attorney, Agent, or Firm*—Klaus J. Bach

[57] ABSTRACT

In a method of diagnosing a malignant disorder or its precursor stage, the percentage parts $N_i$ of blood cells in a size range of $i=6$ μm to $i=16$ μm in two blood samples of a patient, an arterial or capillary blood sample (A) and a venous blood sample (V) are determined based on the total number of blood cells in the arterial or capillary blood sample and the venous blood sample, the values obtained thereby a multiplied by a weighting factor $\alpha_1$ and are then summed up and from the sums A and V, respectively the values $x=A+V$ and $y=A-V$ are calculated and the deviation of the values x and y from the values x and y of a healthy person are determined for diagnosing the disorder.

2 Claims, 2 Drawing Sheets

METHOD OF DIAGNOSING A MALIGNANT DISORDER OR ITS PRECURSOR STAGES

This is a continuation-in-part of PCT/EP96/04416 filed Oct. 11, 1996.

BACKGROUND OF THE INVENTION

The invention relates to a method of diagnosing a malignant disorder or its precursor stages by a blood test.

For the diagnosis of malignant disorders imaging methods (x-ray, ultrasound, computer tomography, core spin tomography), histological examinations of biopsy materials, antibody tests and tests for more or less specific tumor markers are utilized. The last mentioned tests are performed with histological preparations as well as with blood samples. The tumor markers are mostly very specific indicating certain types of tumors.

The main problem is that these procedures, depending on the state of the disorder, have generally an unsatisfactory hit quota, that is, they are not very reliable and can distinguish only insufficiently between malignant and benign forms or respectively, precursor stages of tumors. Some of the imaging methods further cause sometimes quite substantial radiation exposure. Biopsy requires an operative procedure which may cause the spreading of tumor cells. In addition, all these procedures are relatively expensive and in some cases reasonably reliable results are obtained only after an evaluation of several days.

The publication "Surgery", Vol. 109 (1991), p. 747–755 describes a study in which the effects of a tumor of the small intestines on the lymphocytes circulating therethrough were to be determined. In this study, patients with a tumor in the small intestines and, as a control group, patients with benign small intestinal disorders and nephrotic defects participated. All patients were operated. From the patients with intestinal tumors arterial and venous blood was taken from the tumor tissue. From the patients of the control group arterial and venous blood was also collected which was taken from the intestinal tissue. The lymphocytes were separated after centrifuging or on the basis of a characteristic volume. The percentage amount of each lymphocyte substitute-population was determined. A particular diagnosis procedure is not reported since the diagnosis was known already before the operation.

The publication Cytometry, Vol. 13 (1992), page 766–774 describes a procedure for recognizing and distinguishing cells of blood smears.

It is the object of the present invention to provide a diagnosis procedure for malignant disorders and their precursor stages which does not additionally stress a patient, which is not based on an imaging procedure, and which can be performed inexpensively and in a simple manner.

SUMMARY OF THE INVENTION

In a method of diagnosing a malignant disorder or its precursor stage, the percentage parts $N_i$ of blood cells in a size range (diameter) of i=6 μm to i=16 μm in two blood samples of a patient, an arterial or capillary blood sample (index A) and a venous blood sample (index V) are determined based on the total number of blood cells in the arterial or capillary blood sample and the venous blood sample, respectively, the values $N_i$ for the size i=6–16 μm obtained thereby are multiplied by a respective weighting factor $\alpha_i$ and are then summed up and from the sums A and V the values X=A+V and Y=A−V are calculated and the deviation of the values X and Y from the values X and Y of a healthy person are determined for diagnosing whether a person is affected by carcinoma corporis uteri or there is a precursor stage or the person is healthy.

With the method according to the invention, peripheral blood cells, preferably the lymphocyte population, are examined. These cells are taken out of a arterial and/or capillary blood sample. The arterial blood can be drawn from a peripheral artery. Instead of arterial blood, capillary blood may be taken as well, for example, blood from a finger tip or blood from an ear lobe of a patient. Generally, either arterial or sapillary blood is taken, but either one or both can be used for determining the lymphocytic population. In addition venous blood is drawn from a patient, for example, from an arm vein.

All the blood samples, that is, the arterial and/or capillary blood as well as the venous blood are examined outside the body. A standard blood smear test is quite suitable. In the test, the size ratios of the cells are determined and then submitted to a mathematical analysis.

For performing the test, blood of an artery and/or capillary blood vessel on one hand and a vein on the other hand is smeared onto a microscope object carrier. The blood cells can be dried fixed and colored by a standard procedure.

Then a size histogram of arterial and/or capillary (index A) and venous (index V) blood cells is established, preferably of the lymphocyte population. This can be done by microscopic measurement of the diameters of a sample of about 200 blood cells, particularly about 200 lymphocytes. To this end, the discrete amount, in % of the total amount of blood cells in the sample, of $(N_i)^A$, or respectively, $(N_i)^V$ in a size range of 6 μm and 16 μm is determined with an accuracy of 1 μm that is, for each size from 6–16 μm (6, 7, 8, . . . 16) such that, for each cell diameter in the range of 6 μm to 16 μm in the arterial or capillary (index A) as well as in the venous blood (index V), the percentage parts $(N_i)^A$ or, respectively, $(N_i)^V$, for i=6 μm to 16 μm of the total member of cells of the respective blood cell sample is determined. There are generally no lymphocytes <6 μm.

DESCRIPTION OF PREFERRED EMBODIMENTS

Figure 1:
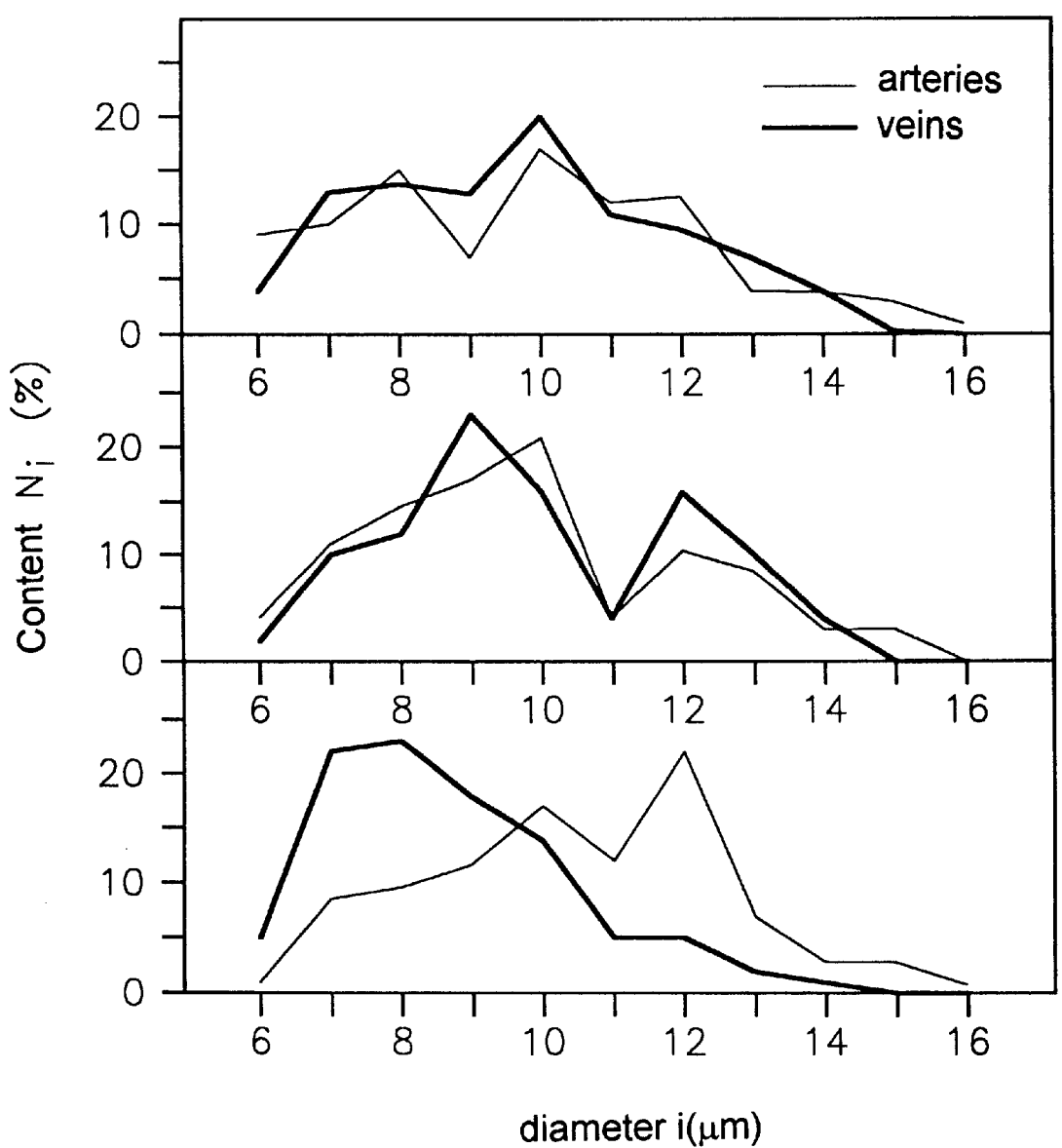
FIG. 1 shows a diagram $(N_i)^A$ and $(N_i)^V$ over i.

As shown in FIG. 1, the values for $(N_i)^A$ and $(N_i)^V$ can be shown graphically as a curve over the cell size i(6 μm≦i≦16 μm). The figure is based on concrete numbers for Ni of various patients and represented in a diagram. The upper part of the figure shows the results (size distribution) for a healthy person, the center part shows the results for a person with fibromyoma and the lower part shows the result for a person with Ca. corporis uteri stage II. With such a diagram, an experienced physician can diagnose the existence of a carcinoma corporis uteri or of a precursor stage thereof or he could exclude the possibility of such a disorder. Clearer results are obtained, however, if the values for $(N_i)^A$ and $(N_i)^V$ are weighted and averaged.

For this purpose, the values $(N_i)^A$ as well as the values $(N_i)^V$ are multiplied each by a specific size-dependent weighting factor α. The weighting factor is normally $2^{10}$ for i=6 μm; for i=6+n μm, the exponent of the weighting factor is reduced preferably by n. In each case, the value of the weighting factor becomes smaller with increasing cell size. Suitable weighting factors α are presented in the table below:

Table:

For i=6 μm: α=$2^{10}$=1024
For i=7 μm: α=$2^9$=512
For i=8 μm: α=$2^8$=256
For i=9 μm: α=$2^7$=128
For i=10 μm: α=$2^6$=64
For i=11 μm: α=$2^5$=32
For i=12 μm: α=$2^4$=16
For i=13 μm: α=$2^3$=8
For i=14 μm: α=$2^2$=4
For i=15 μm: α=$2^1$=2
For i=16 μm: α=$2^0$=1

Then the following sums are formed:

$$A = \Sigma\, \alpha_i \cdot (N_i)^A$$

$$V = \Sigma\, \alpha_i \cdot (N_i)^V$$

From the sums A and V, the linear combinations:

$$X = A+V, \text{ and}$$

$$Y = A-V$$

are calculated.

Figure 2:
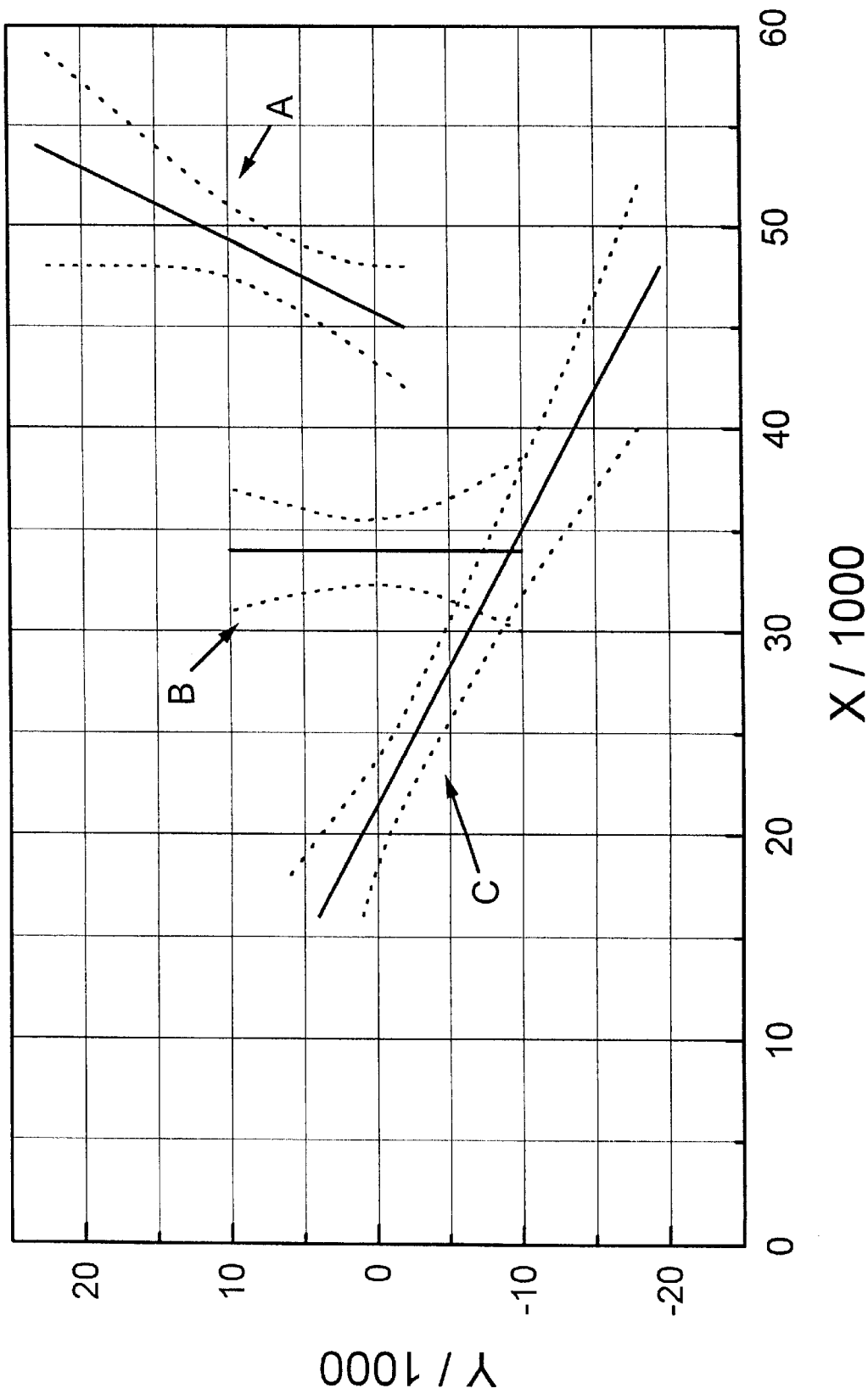
FIG. 2 represents a coordinate system which permits a diagnosis.

As shown in FIG. 2, the values X and Y can be presented as point coordinates in a plane. The representation in a coordinate system immediately permits a diagnostic coordination since, during the examination of a large number of patients, an arrangement of coordinate ranges was found to exist for the various disorders. The ranges "healthy" (A) to a benign form or precursor stage (B) and further up to the malignant form (carcinoma corporis uteri of different seriousness) (C) are presented in a clearly distinctive way in the coordinate system. The data for FIG. 2 were gathered by examination of a foreign population. The full lines represent the average values; the dashed lines represent the 95% coverage range.

The invention has the advantage that the diagnosis can be made on the basis of blood which is generally drawn anyhow. The method according to the invention therefore represents no additional stress to the patient. The success quota of the method is higher than 95% as has been proven by preliminary tests. The method requires no expensive equipment so that the method can be performed anywhere, also in regions where sophisticated technical equipment is not available. The tests can be performed normally using a microscope; an automation of the testing procedure with relatively inexpensive equipment is possible. Of course, the method according to the invention is suitable for large scope preventative examinations since it is relatively inexpensive.

The invention will now be described on the basis of an example:

From standard blood smears of arterial and venous blood of three patients, the percentage parts ($N_i$) are determined for each lymphocyte size in the range of 6 μm to 16 μm by observation under the microscope. The size distribution diagram is represented in FIG. 1.

The values for $(N_i)^A$ and $(N_i)^V$ are multiplied by the respective weighting factors and summed up. For the linear combination X=A+V and Y=A-V the following values are obtained:

Control value (healthy person) X=40762, Y=+3200

Patient with fibromyoma X=32810, Y=+2538

Patient with Ca. Corp. w. II X=39361, Y=-15927

Particularly outstanding is the high negative value for Y for the patient with Ca. corporsi uteri, stage II.

What is claimed is:

1. A method of diagnosing carcinoma corporis uteri or its precursor stage comprising the steps of:

a) providing two blood samples of a patient, one comprising at least one of arterial and capillary blood (index A) and the other comprising venous blood (index V);

b) measuring, in increments of 1 μm, blood cells in the size range of i=6 μm diameter to i=16 μm diameter, and determining the number of cells that fall within said range in index A and also in index V to the total number of cells in index A and index V to obtain a percentage part value ($N_i$) for each index;

c) multiplying the obtained blood cell percentage part values by a weighting factor $\alpha_i$, wherein $\alpha_i$ is $2^{10}$ for i=6 μm, $2^9$ for i=7 μm, $2^8$ for i=8 μm, $2^7$ for i=9 μm, $2^6$ for i=10 μm, $2^5$ for i=9 μm, $2^4$ for i=12 μm, $2^3$ for i=13 μm, $2^2$ for i=14 μm, $2^1$ for i=15 μm and $2^0$ for i=16 μm;

d) then calculating sums for each index by:

$$A = \Sigma\, \alpha_i^*(N_i)^A$$

$$V = \Sigma\, \alpha_i^*(N_i)^V$$

e) calculating values X=A+V and Y=A-V, and f) comparing the calculated X and Y values to value ranges obtained from healthy controls, precursor stage controls, and carcinoma controls, wherein, carcinoma corporis uteri are indicated if the calculated values fall within the range determined for carcinoma controls, precursor stage carcinoma corporis uteri are indicated if the calculated values fall within the range determined for precursor controls, and absence of a carcinoma is indicated if the calculated values fall within the range determined for healthy controls.

2. A method according to claim 1, wherein lymphocytes are used as blood cells, and the number of lymphocytes is used as the total number of blood cells.

* * * * *